United States Patent [19]

Weiss

[11] 4,228,514
[45] Oct. 14, 1980

[54] METHOD AND SYSTEM FOR DETERMINING THE WEAR OF A DRILL BIT IN REAL TIME

[75] Inventor: Roger E. Weiss, Denville, N.J.

[73] Assignee: Bell Telephone Laboratories, Incorporated, Murray Hill, N.J.

[21] Appl. No.: 30,061

[22] Filed: Apr. 16, 1979

[51] Int. Cl.³ ................. G01N 19/00; G06F 15/46
[52] U.S. Cl. ................................. 364/551; 364/508; 364/475; 73/104
[58] Field of Search .............. 364/475, 474, 111, 551; 73/104

[56] References Cited

U.S. PATENT DOCUMENTS

| | | | |
|---|---|---|---|
| 3,694,637 | 9/1972 | Edwin et al. | 364/508 |
| 3,819,916 | 6/1974 | Watanabe | 73/104 X |
| 3,834,615 | 9/1974 | Watanabe et al. | 364/475 X |
| 3,841,149 | 10/1974 | Edwin et al. | 364/508 X |
| 3,841,198 | 10/1974 | Cornford | 364/475 X |
| 3,848,115 | 11/1974 | Sloane et al. | 364/508 |
| 3,872,285 | 3/1975 | Shum et al. | 73/104 X |
| 3,920,971 | 11/1975 | Bevis et al. | 364/560 |
| 3,961,184 | 6/1976 | Schurrer | 250/231 |
| 3,987,670 | 10/1976 | Tuzzeo et al. | 73/104 |
| 4,023,044 | 5/1977 | Miller et al. | 307/116 |
| 4,030,201 | 6/1977 | Possati et al. | 364/560 X |
| 4,120,196 | 10/1978 | Hamilton et al. | 73/104 |
| 4,176,396 | 11/1979 | Howatt | 364/111 X |

OTHER PUBLICATIONS

Automotive and Aviation Industries, May 15, 1942, vol. 86, pp. 30–34, Metal-Cutting Forces and Power Requirements for Machine Tools.
Tool Engineers Handbook, 1959, 2nd Edition, McGraw-Hill Book Co., pp. 18-43 through 18-48.
Journal of Engineering for Industry, May 1977, pp. 295–301, Sensing of Drill Wear and Prediction of Drill Life.

Primary Examiner—Edward J. Wise
Attorney, Agent, or Firm—John W. Fisher

[57] ABSTRACT

A method and a system are disclosed for determining the wear of a drill bit in real time. At a predetermined point prior to engagement of the drill bit with the workpiece, a first rotational speed of the drill bit is ascertained. Upon exit of the drill bit from the workpiece a second rotational speed is determined. Measurement of these two rotational speeds enables a determination to be made of the loss of energy resulting from the drilling operation. This loss in energy is used to produce a measure of drill bit wear.

21 Claims, 15 Drawing Figures

FIG. 6
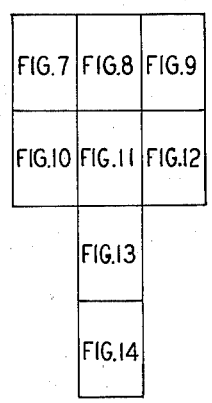
FIG. 15
```
CSR0  CSR1  D015
 0     0     0    LOAD ADDRESS REG
 0     0     1    LOAD # OF SPINDLE REVOLUTIONS
 0     1     0    LOAD HEIGHT REG
 0     1     1    MEASURE PERIOD
 1     0     0    LOAD DISPLAY
 1     0     1    RESET CLOCK
 1     1     0⎤   DRILL POWER ON/OFF
 1     1     0⎦   DIAGNOSTIC   ON/OFF
```
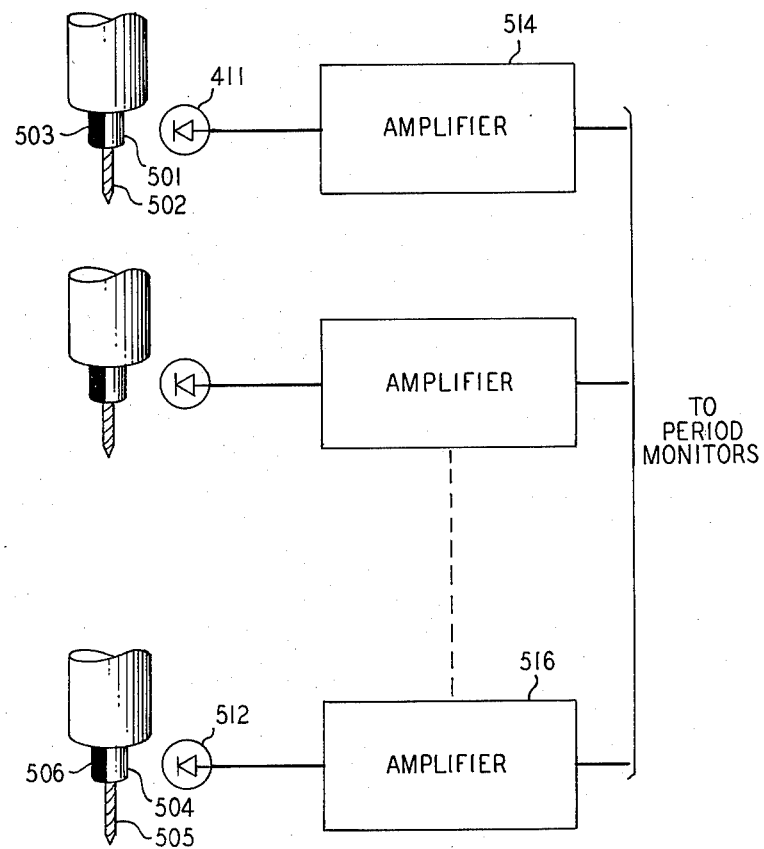
FIG. 7

METHOD AND SYSTEM FOR DETERMINING THE WEAR OF A DRILL BIT IN REAL TIME

BACKGROUND OF THE INVENTION

1. Technical Field of the Invention

This invention relates to machine tools, and more specifically, to machine tools that include means for automatically controlling their operation.

2. Description of the Prior Art

In the fabrication of numerous commercial products, oftentimes it is necessary to drill precise holes in the product. For example, in fabricating multilayer printed circuit boards, the drilled holes must be of sufficient quality to permit the plating of a thin layer of copper about the hole periphery. Any projections or rough edges around the hole periphery may result in inadequate plating thickness or plating uniformity. These inadequacies, in turn, could lead to failure of the printed circuit board and the equipment of which it is a part.

Drilling operations which are to be carried out on items to be mass produced are frequently undertaken by multiple spindle drilling machines having automatic workpiece advance mechanisms built into them. As the workpiece is fed beneath the drill spindles, the spindles are lowered and raised cyclically so that the drilling operation can be implemented in as nearly an automatic process as possible. One problem, however, in undertaking drilling operations in this manner is that drill bits can lose their sharpness or in fact become broken before an operator can detect such a condition. As a result several workpieces could be ruined.

In a paper entitled "Metal-Cutting Forces and Power Requirements for Machine Tools" by O. W. Boston appearing in *Automotive and Aviation Industries*, Volume 86, May, 1942 at page 32, there is an indication that a dynamometer may be used on a lathe or planer in such a manner as to determine the tangential cutting force alone or the three components (tangential, longitudinal, and radial) of the cutting force.

A generalized description entitled "Relationship of Forces and Power Consumption to Machine Variables" appears in *Tool Engineers Handbook* 2nd Edition published by McGraw-Hill Book Company, Copyright 1959 at pages 18-43 and 18-44. In particular, it is noted that power consumption in a machining operation is roughly proportional to the cutting speed, since the rate at which metal is removed is proportional to that speed. It is further noted that the effect of cutting speed on certain tool forces depends upon a number of factors including the tool-work combination, tool geometry, speed range involved, feed, depth of cut, and type of machining operation. Unfortunately, both of the aforementioned references are devoid of any suggestion of a method or apparatus for determining the wear of a drill bit in real time.

A reference which addresses the problem of monitoring rotating parts is U.S. Pat. No. 3,961,184 issued June 1, 1976 to J. Schurrer. Schurrer relates to a device for making photoelectric measurements of moving parts. The moving part is provided with contrast markings thereon and a source of light is directed onto the contrast marks. Light reflected from the moving part is picked up by a receiver and the periodic sensing of this light can be translated into a measurement of rotational speed of the moving part. While Schurrer represents an advance in the art of monitoring moving parts, there is no suggestion of a solution to the problem of detecting when a drill bit either loses sharpness or becomes broken.

A more recent advance in automatic monitoring systems is disclosed in R. C. Miller et al, U.S. Pat. No. 4,023,044 issued May 10, 1977. Miller et al disclose a monitoring system comprised of a transducer mounted in association with a machine tool for producing a signal in response to mechanical impulses developed by operation of the machine tool. The signal is detected and applied to the input of means for generating a test function. This test function is a function of both the time and the amplitude of the transducer signal. Means are provided for producing a reference function proportional to the test function evaluated during normal operation of the machine tool and for comparing this reference function with the test function evaluated during subsequent operations. A comparator generates an output signal for controlling operation of the machine tool when the test function and the reference function differ by more than a predetermined amount. Even with this advance the Miller et al reference falls short of the mark for providing a solution to the problem of determining the wear on a machine tool, such as a drill bit, in real time.

In view of the foregoing, is should be apparent that a number of problems have not been addressed by the prior art. Specifically, none of the references deals with a way to monitor the quality of a drill bit and a drilled hole in real time. Moreover, the problem associated with the detection of broken drill bits has not been considered, even remotely. Still other problems requiring solution are those related to providing an indication when the drill bit quality dips below a standard so that the drill bit can be changed; ways to limit the amount of energy expended in a drilling operation; methods to ascertain the drillability of various types of material; and methods to evaluate the quality of drills supplied by different manufacturers.

SUMMARY OF THE INVENTION

The foregoing problems are greatly alleviated in accordance with my invention. One illustrative embodiment of the invention comprises a method for ascertaining the wear of a drill bit during the performance of a drilling operation on a workpiece. In implementing the method, a position of the drill bit is monitored prior to engagement with the workpiece. At a position indicated by the position monitoring device, a first rotational speed of the drill bit is determined. This first rotational speed is stored and then a second rotational speed of the drill bit is determined. This second speed determination occurs at a position indicated by the position monitoring device following emergence of the drill bit from the workpiece. Based on the measurements of the first and second rotational speeds and the elapsed time between these measurements, the amount of energy expended in the drilling operation can be ascertained. From this energy a measure of the wear on the drill bit can be generated.

Numerous advantages are to be derived from the practice of this method. For example, worn or broken drill bits can be detected; the monitoring of drilling operations to ascertain worn or broken bits can be advantageously performed in real time; drill bit monitoring can be used advantageously to optimize the feed rate and spindle speed of the drilling process; certain diagnostic information can be advantageously provided to an operator; storage and correlation of expended energy can be used to facilitate lot inspection of products produced by the drilling operation; and the age of a drill bit can be monitored.

BRIEF DESCRIPTION OF THE DRAWINGS

The aforementioned advantages of the invention as well as other advantages will be better understood upon a consideration of the following detailed description and the appended claims taken in conjunction with the attached drawings of an illustrative embodiment in which:

FIG. 6 is a layout of FIGS. 7 through 14;

FIGS. 7 through 14 when interconnected in accordance with the layout of FIG. 6 illustrate the real time monitoring circuits; and FIG. 15 is a table indicating various functions to be implemented in accordance with specified signal states.

DETAILED DESCRIPTION

Figure 1:
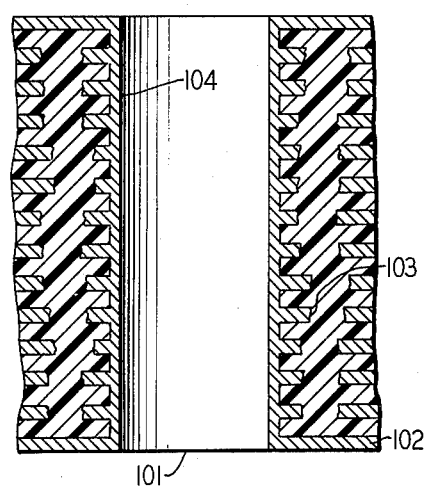
FIG. 1 illustrates a hole drilled in a multilayer printed circuit board with a high quality, sharp drill bit.

Throughout the detailed description reference will be made to various elements shown in the drawings. The first one or two numerals in each reference character denote the figure wherein the referenced element is first illustrated. For example, drilling machine spindle 501 is first illustrated in FIG. 5. Similarly, decoder 1210 is first illustrated in FIG. 12. Utilization of this format should make it easier for the reader to follow the detailed description.

1.0 GENERAL DISCUSSION

Illustrated in FIG. 1 is a photomicrograph of a high quality plated-through-hole 101 in a multilayer printed circuit board 102. Hole 101, prior to plating, was drilled with a sharp drill bit. Consequently, no damage has been effected to land areas 103. In addition, sidewall 104 is smooth and uniform throughout the length of hole 101. Plated-through-holes of this quality are desired in the manufacture of any multilayer printed circuit board 102.

Figure 2:
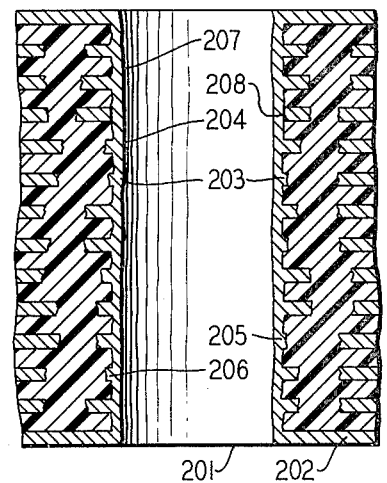
FIG. 2 illustrates a hole drilled in a multilayer printed circuit board with a drill bit of poor quality.

In contrast, the photomicrograph illustrated in FIG. 2 shows a low quality plated-through-hole 201 in a similar multilayer board 202. It should be apparent from this illustration that plated-through-hole 201 has a number of defects including land tear-out, epoxy smear and sidewall roughness. Each of these defects will be discussed briefly in the following paragraphs.

With respect to land tear-out, this drilling defect occurs when the bond between the epoxy and the copper land is weakened due to excessive heat generated by a worn drill bit as the drill bit cuts through the land. The entire land is pulled into the hole leaving a large void in the sidewall. During plating, copper will not easily fill this void and a mechanically weak barrel can result. As shown in FIG. 2, circuit land 203 has been completely destroyed during the drilling operation and lands 204 through 206 have been partially destroyed. Destruction of lands 203 through 206 during the drilling operation could render plated-through-hole 201 functionally useless.

Epoxy smear, as the name suggests, is a layer of epoxy which has been smeared over the sidewall during the drilling operation. Epoxy smear results because when a drill bit cuts into the epoxy material to produce a hole, chips of epoxy are produced and heat is generated. The heat generated during the drilling operation causes these chips to melt and smear across the copper layer in sidewall 207 as illustrated at land 208. This smear of epoxy formed over the edge of the land area, if not removed during subsequent cleaning operations, will insulate land 208 from the barrel of plated-through-hole 201 as it is formed during subsequent copper plating operations.

The roughness in sidewall 207 of plated-through-hole 201 results from the roughness produced by a poor quality drill bit during the drilling operation. A hole having rough sidewalls as a result of poor quality drilling will have rough sidewalls after the plating operation. This roughness in the sidewall can cause locally thin copper during plating which, in turn, may result in stress concentrations and barrel cracking during soldering operations. The end result is that plated-through-hole 201 is unable to meet generally applicable reliability standards.

Figure 3:
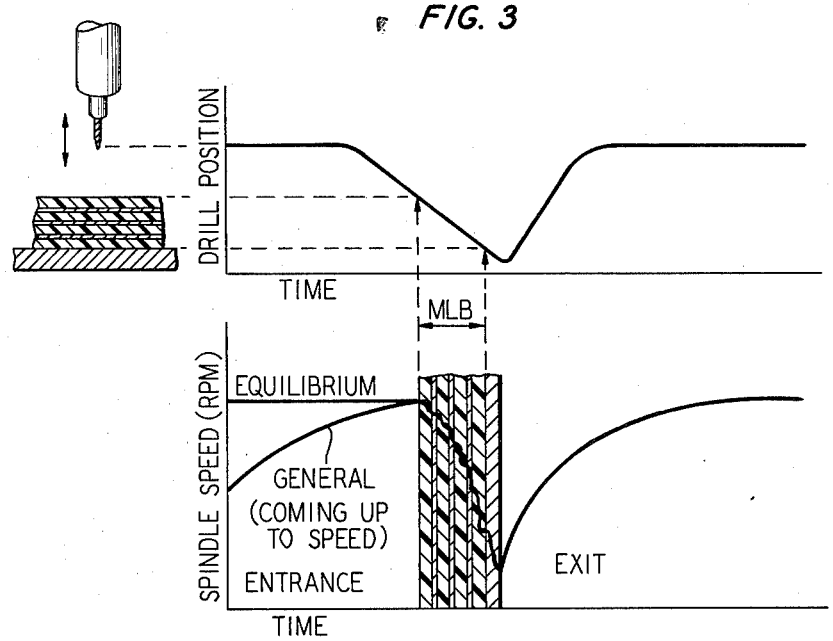
FIG. 3 is a plot of speed versus time and position versus time illustrating the change in speed of a drill bit as it engages a workpiece.

FIG. 3 represents a graphical description of the drilling operation in a general sense. The upper curve shows drill position as a function of time. Initially, the drill bit is held in a rest position well above the workpiece. At some later time the drill bit is lowered toward the workpiece. This is illustrated by the downwardly sloped portion of the curve. Once the drill bit is brought into engagement with the workpiece, it continues its downward motion as it cuts through the workpiece to form the hole. After the hole is formed the drill bit is withdrawn. This is illustrated by the upwardly sloped portion of the curve. It continues in the upward direction until the drill bit returns to its rest position.

Having considered graphically drill position versus time it will be helpful to consider graphically variations in spindle speed versus time. In a situation where the drill bit is allowed to remain at its rest position for a substantial period of time, the spindle speed will be at a constant level illustrated by the equilibrium line in the bottom curve of FIG. 3. Assuming this to be the case, once the drill bit is brought into engagement with the workpiece, the spindle speed rapidly falls off as it cuts deeper and deeper into the workpiece. Depending on the thickness of the workpiece and the physical properties of the various layers within the workpiece, other speed variations will occur until at some point the drill bit exits from the workpiece. At this point the spindle speed will gradually increase and return to an equilibrium condition.

While this description is useful in understanding the drilling process, it is not representative of the variations in spindle speed which are encountered at a drilling facility in a manufacturing plant. In the latter situation, the drill bits are repeatedly engaging the workpiece in what might be characterized as a "pecking away" type of operation. Consequently, seldom if ever is the spindle speed allowed to return to an equilibrium state. As a result, in most instances the spindle speed is gradually building up to its equilibrium state at the time it engages the workpiece.

The significance to be derived from this lies in the fact that if the spindle speed were always initially in an equilibrium state prior to engagement with the workpiece, changes in the power delivered to the spindle could be measured and integrated to arrive at the amount of energy needed to drill the hole. Unfortunately, because equilibrium is seldom, if ever, encountered in real life situations and because of inherent delays reflecting changes in power consumed, this approach is not feasible. To circumvent these limitations in measurement capability some other approach must be utilized.

In accordance with the subject invention if certain spindle parameters, such as frictional losses and the like, can be ascertained before the drilling event, then changes in spindle speed resulting from the drilling operation can be advantageously utilized to generate a measure of the energy expended in the drilling operation.

Figure 4:
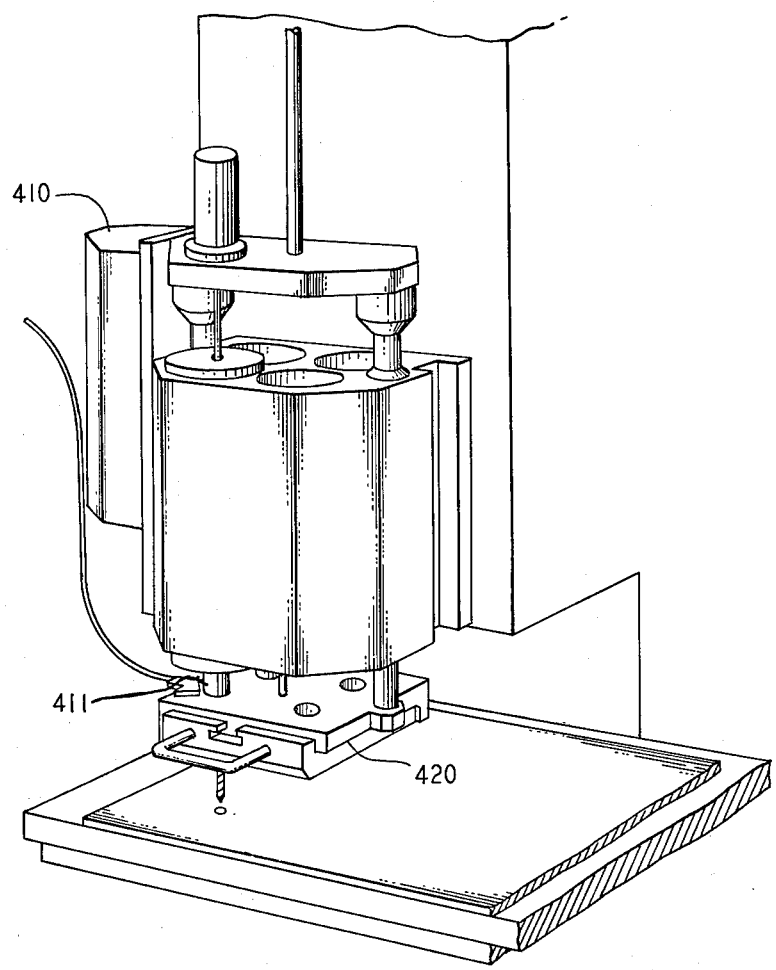
FIG. 4 is a simplified illustration of the machine instrumentation.

To facilitate measurement of changes in spindle speed, which changes must be measured accurately with respect to the position of the drill bit and the workpiece, an arrangement such as that illustrated in FIG. 4 is utilized. Affixed to the drilling machine is a Z-axis monitor 410, such as a model 500-LR spar and transducer manufactured by Quality Measurement Systems, Inc. Monitor 410 permits an accurate measure of the position of the drill bit with respect to the workpiece. By setting Z-axis monitor 410 such that it generates an output signal at a predetermined position just above the workpiece, a phototransistor-photodiode pair 411, such as a type OPB 253A reflective object sensor manufactured by Optron, Inc., can be triggered advantageously at the position sensed by monitor 410 to measure the change between the spindle speed just prior to engagement of the drill bit with the workpiece and just after the drill bit exits from the workpiece. With this measurement of the change in spindle speed, the elapsed time between the two measurements, and having previously ascertained various spindle characteristics, such as frictional losses, the moment of inertia of the spindle and the like, the amount of energy expended in drilling the hole can be advantageously ascertained in real time. Once the amount of energy is ascertained, various quality measures for both the hole drilled and the drill bit can be inferred.

2.0 OVERVIEW OF SYSTEM OPERATION

Figure 5:
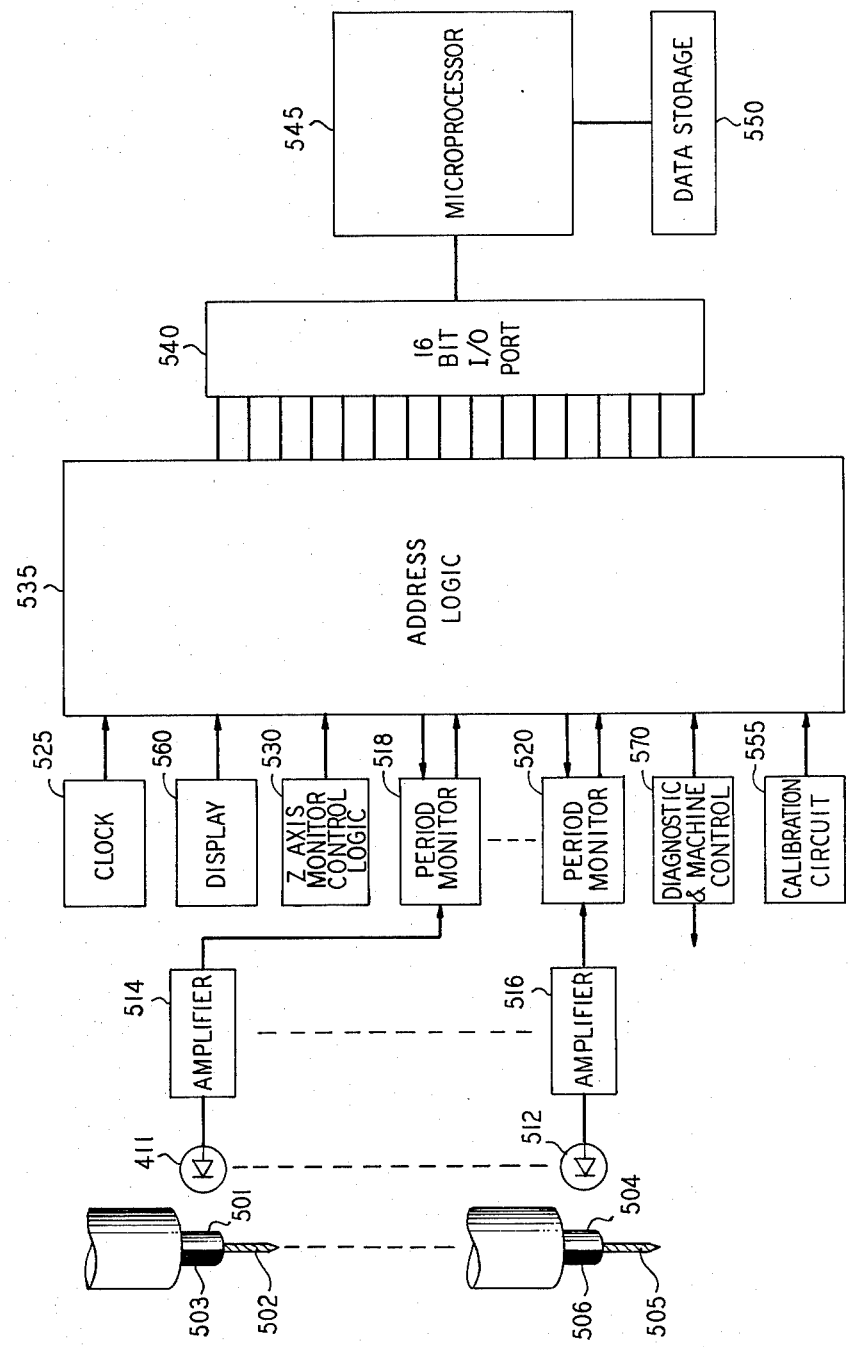
FIG. 5 is a simplified block diagram illustrating the monitoring system and the flow of information therein.

As illustrated in FIGS. 5 and 7, drilling machine spindle 501 has affixed therein drill bit 502. Extending approximately halfway around the circumference of spindle 501 is a black stripe 503. Similarly, drilling machine spindle 504 has affixed therein drill bit 505. Spindle 504 includes a black stripe 506. Although only two spindles are shown, as many as n spindles can be advantageously accommodated. In one embodiment of the system n is 16.

As spindle 501 rotates, black stripe 503 is illuminated by photodiode-phototransistor pair 411. When the incident light impinges on black stripe 503, most of it is absorbed. However, when the incident light impinges on the shiny surface juxtaposed black stripe 503, a considerable portion of the light is reflected and detected by photodiode-phototransistor pair 411. This reflected light, upon detection by photodiode-phototransistor pair 411, produces an output roughly approximating a square wave. The period of this square wave is proportional to the period of rotation of spindle 501. The detected signal is applied to amplifier 514 which amplifies the signal and also performs wave shaping to square up the leading and trailing edges of the signal to form a good approximation of a square wave.

The signal from amplifier 514 is routed to period monitor 518. Period monitor 518 in turn is coupled via address logic 535 to clock 525. For j square pulses out of amplifier 514, clock 525 generates k clock pulses. These clock pulses are accumulated in period monitor 518. From the measurement of the period of rotation of spindle 501 by period monitor 518 the rotational speed of spindle 501 can be obtained. The rotational speed in revolutions per minute (rpm) is proportional to the reciprocal of the period as ascertained by period monitor 518. In a similar fashion, photodiode-phototransistor pair 512 in conjunction with amplifier 516 and period monitor 520 obtain corresponding period information with respect to the $n^{th}$ spindle. Hereinafter all further discussion will be confined to a single spindle 501 and its associated electronics.

The point at which period monitor 518 is actuated to affect a measurement of the rotational period of spindle 501 is controlled by Z-axis monitor control logic 530. To provide flexibility to accommodate various types of workpieces, the point at which Z-axis monitor control logic 530 is actuated is flexibly controlled by microprocessor 545. Microprocessor 545 feeds the operator-selected control height and directional information through input/output port 540 and address logic 535 to Z-axis monitor control logic 530. As noted, both height and directional information are utilized. The directional information indicates whether spindle 501 is being lowered or raised.

When spindle 501 reaches the preselected height above the workpiece, Z-axis monitor control logic 530 produces a pulse which is coupled via address logic 535 and input/output port 540 to microprocessor 545. Microprocessor 545 in turn sends a signal back to period monitor 518 to initiate measurement of the rotational speed. If this is the first measurement of rotational speed, another signal is sent from microprocessor 545 to clock 525 setting it to zero.

After period monitor 518 completes its measurement, a pulse is sent to microprocessor 545 that the measurement is complete. Microprocessor 545 than takes a reading of the data in period monitor 518. At this point microprocessor 545 sets the next height into Z-axis monitor control logic 530.

In general three different rotational speed readings are obtained at three different positions. The first reading is obtained at a position which indicates drill bit 502 to be on its way down toward the workpiece. The second reading is obtained at a position just before drill bit 502 engages the workpiece. The third reading is obtained at a position where drill bit 502 exits from the workpiece. During the measurements made at the second and third positions, clock 525 is not reset. Instead a reading of time is coupled from clock 525 to microprocessor 545. In addition, a reading of rotational speed is coupled from period monitor 518 to microprocessor 545. Hence, a rotational speed is obtained at three specific positions and time information is obtained with respect to the latter two positions with the first position time being set at zero. From this data and calibration data obtained from calibration circuit 555, a determination of the energy expended in drilling a hole can be advantageously ascertained.

The drilling energy is obtained by an approximation to the solution of the differential equation which describes the motion of drill spindle 501. This solution is given by $$E = \tfrac{1}{2}I\{2\omega_1 A - A^2\},$$

where $$A = \frac{C\Delta t\{(\omega_0 - \omega_1) - (\omega_0 - \omega_2)e^{C\Delta t}\}}{\{1 - e^{C\Delta t}\}};$$

E = drilling energy;
I = spindle moment of inertia;
$\omega_0$ = equilibrium rotational speed in radians per second;
$\omega_1$ = rotational speed at the entrance to the hole in radians per second;
$\omega_2$ = rotational speed at the exit from the hole in radians per second;
C = spindle calibration constant; and
$\Delta t$ = elapsed time between the measurement of $\omega_1$ and $\omega_2$.

At this point it should be noted that the n spindles are raised and lowered as a group. Moreover, it should be noted further that those spindles actually used for drilling a hole are lowered to a greater extent than those spindles not being used for drilling holes. If a given spindle is lowered so as to effect a drilling operation, a rotational speed measurement can be made. If a particular spindle is not to be used to effect a drilling operation, no rotational speed measurement can be made and no data manipulation is required. This result obtains because photodiode-phototransistor pair 411 is affixed to pressure foot 420 and it is only if a given spindle reaches pressure foot 420 that rotational speed measurements can be effected.

Assuming that the energy inferred is zero, as a result of the measurements effected at the second and third positions, then it follows that no hole was drilled. This in turn indicates that the drill bit that was to be used to drill a hole is broken. On the other hand, if the energy exceeds some predetermined limit, than it can be inferred that the drill bit is worn excessively.

From the measured time information and knowing the heights at which the data was collected, the feed rate of the drilling operation can be obtained. Once the feed rate is ascertained this information, along with the rotational speed of the spindle as previously determined at measurement position one, is presented to an operator on display 560. Additional information which is presented on display 560 includes the spindle identification, the number of holes drilled with that spindle, the amount of energy expended in drilling the most recent hole with that spindle, and certain diagnostic information.

By keeping track of the feed rate, one is able to obtain an average feed rate for an entire run. Moreover, by keeping track of the number of times that a given drill bit goes up and down, one is able to obtain the number of machine cycles. This ability to monitor the feed rate is a spin-off benefit which enhances overall process control. Once an optimum feed rate has been ascertained for optimum hole quality, accurate process control can be advantageously maintained.

Data storage 550 is provided to record information such as the amount of energy required to drill each hole, the average feed rate and the average spindle speed. This data is subsequently used for process optimization and quality control purposes.

If spindle 501 is idling, that is, not being used in a drilling operation for approximately three seconds or so, spindle 501 is considered to be at its equilibrium speed. This equilibrium speed is used as part of the calibration data to obtain the measure of energy expended during a drilling operation. In the event the selected time interval has elapsed, the speed measurement at position one is used as the equilibrium speed. On the other hand if the time interval has not elapsed, the previous equilibrium speed measurement is used as an indication of the present equilibrium speed. It should be noted that this approximate three second interval is adjustable.

Each time a drilling energy measurement is obtained, it is compared with predetermined limits. If the energy falls within the limits, nothing happens. If the measured energy falls outside the limits, microprocessor 545 puts this information on display 560 in blinking fashion along with an indication of the nature of the problem. When a problem is detected, diagnostic and machine control logic 570 stops the machine.

At this point it should be noted that calibration is done separately from the actual drilling process data collection. During calibration, data from Z-axis monitor control logic 530 is ignored. To effect the calibration, calibration circuit 555 cuts power to the spindle drive allowing spindle 501 to slow down. This permits the measurement of spindle viscous wind loss. When power is restored, a measure of the restoring torque is obtained. This measurement of both the wind loss and restoring torque are obtained from speed measurements and time data derived from period monitor 518 and clock 525. The moment of inertia of spindle 501 is obtained by virtue of a torsional pendulum method which utilizes a calibrated wire one end of which is fastened to the spindle and the other end of which is fastened to a fixed point.

3.0 DETAILED CIRCUIT OPERATIONS

3.1 Period Monitor

Figure 13:
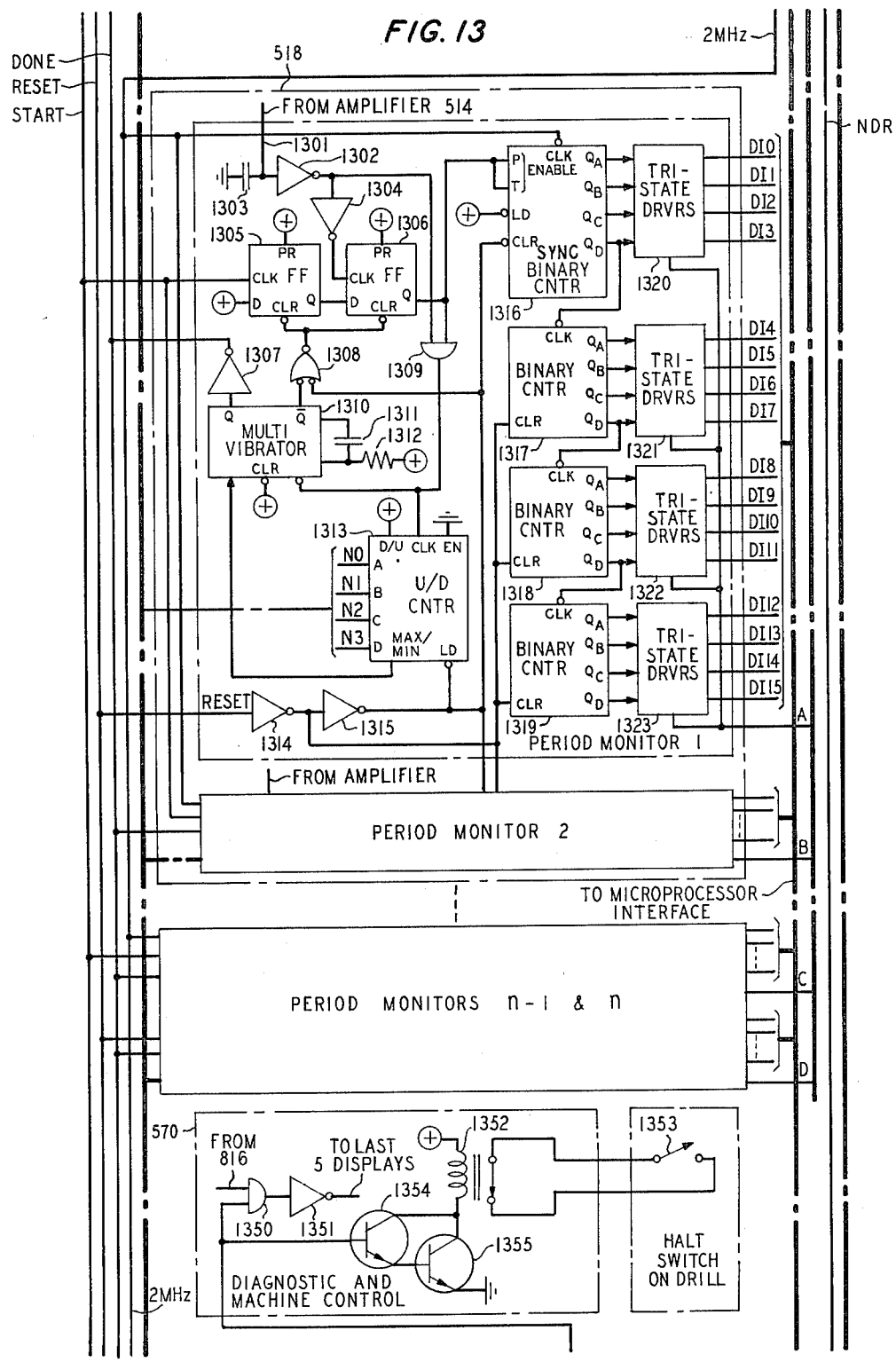

Period monitor 518, as shown in detail in FIG. 13, is one of the basic circuits used to obtain rotational speed information. To obtain this information the shaped square wave from amplifier 514 is fed via lead 1301 to an inverter 1302, such as a Texas Instruments, Inc. hex schmitt-trigger inverter model SN7414. In addition to inverting the waveform, inverter 1302 provides some degree of isolation, and along with capacitor 1303, it serves to filter out any high frequency noise which may be coupled onto circuit 1301.

At this point microprocessor 545 provides a reset pulse on a lead labeled RESET to inverters 1314 and 1315. Inverter 1314, in addition to inverting the reset pulse, facilitates fan out of this signal to other period monitors within the system. Following inversion of the reset pulse in inverter 1314, it undergoes a further inversion in inverter 1315. The signal out of inverter 1315 is applied to the LD input of up/down counter 1313, such as a model SN74LS191 counter manufactured by Texas Instruments, Inc., thereby enabling counter 1313 to load in the binary value of the number of revolutions to be sampled. This information appears on leads N0 through N3.

The signal out of inverter 1315 is coupled via NOR gate 1308 to the CLR inputs of flip-flops 1305 and 1306 thereby forcing their Q outputs to zero. Binary counter 1316 is also set to zero by the application of the reset pulse from inverter 1315.

The signal from inverter 1314 is applied to the CLR inputs of binary counters 1317 through 1319 thereby resetting these counters. Examples of binary counters which are suitable for this purpose are models SN74393 and SN74LS161 counters manufactured by Texas Instruments, Inc.

Once counters 1316 through 1319 are reset, microprocessor 545 sends out a pulse on a lead labeled START. This pulse is applied to the CLK input of a flip-flop 1305, such as a model SN74LS74 flip-flop manufactured by Texas Instruments, Inc., and causes the Q output to change to a high logic level. The high logic level is applied to the D input of flip-flop 1306. At this point period monitor 518 is ready for the first pulse transition to be generated by the rotation of spindle 501. When a pulse transition occurs, the signal indicating this transition is applied via amplifier 514 and inverters 1302 and 1304 to the CLK input of flip-flop 1306 causing its Q output to go to a high logic level.

With the Q output high on flip-flop 1306, AND gate 1309 is enabled for gating additional pulse transitions. An example of an AND gate suitable for this purpose is a model SN7408 gate manufactured by Texas Instruments, Inc.

The high logic level applied to AND gate 1309 also enables binary counters 1316 through 1319. Once counters 1316 through 1319 are enabled, the two megahertz clock signal can be counted. Upon the occurrence of the first pulse transition the output from AND gate 1309 goes to a high logic level. This signal is applied to the CLK input of up/down counter 1313 causing a down count by one. For each additional spindle rotation, up/down counter 1313 is decremented until the number of revolutions previously set in is reached.

When up/down counter 1313 reaches zero, a pulse appears on the max/min output. This signal is applied to a multivibrator 1310, such as a Texas Instruments, Inc. model SN74LS221, which generates two pulses one of which is inverted in inverter 1307 and fed over a lead labeled DONE to Z-access monitor control logic 530. The other pulse is coupled via NOR gate 1308 to flip-flops 1305 and 1306 causing them to be cleared. Control of these pulse widths is effected by capacitor 1311 and resistor 1312. With flip-flops 1305 and 1306 cleared, AND gate 1309 is disabled preventing further rotational counts to enter up/down counter 1313. In addition, binary counters 1316 through 1319 are disabled.

The number of clock pulses contained in j revolutions of spindle 501 are now contained in counters 1316 through 1319. This information is subsequently coupled out on leads QA through QD of counters 1316 through 1319. Since there are four counters in the chain, a 16-bit binary number is available to indicate the number of clock pulses contained in the j spindle revolutions.

The pulse appearing on the lead labeled DONE is fed to Z-axis monitor control logic 530 and, in particular, to flip-flop 1033 therein causing it to change state. This change in state is fed via tristate drivers 1036, such as Texas Instruments, Inc. model SN74367, to a REQ B input of input/output port 540. Upon receipt of the REQ B pulse, microprocessor 545 couples a signal through address logic 535 to period monitor 518. This signal causes the sequential loading of the outputs of binary counters 1316 through 1319 into tristate drivers 1320 through 1323 and thence to input/output port 540 and microprocessor 545.

At this point data is available on the number of revolutions of one spindle 501 at one measurement point. Other period monitors 518 simultaneously collect similar data from other spindles on the drilling machine.

3.2 Clock

Figure 8:
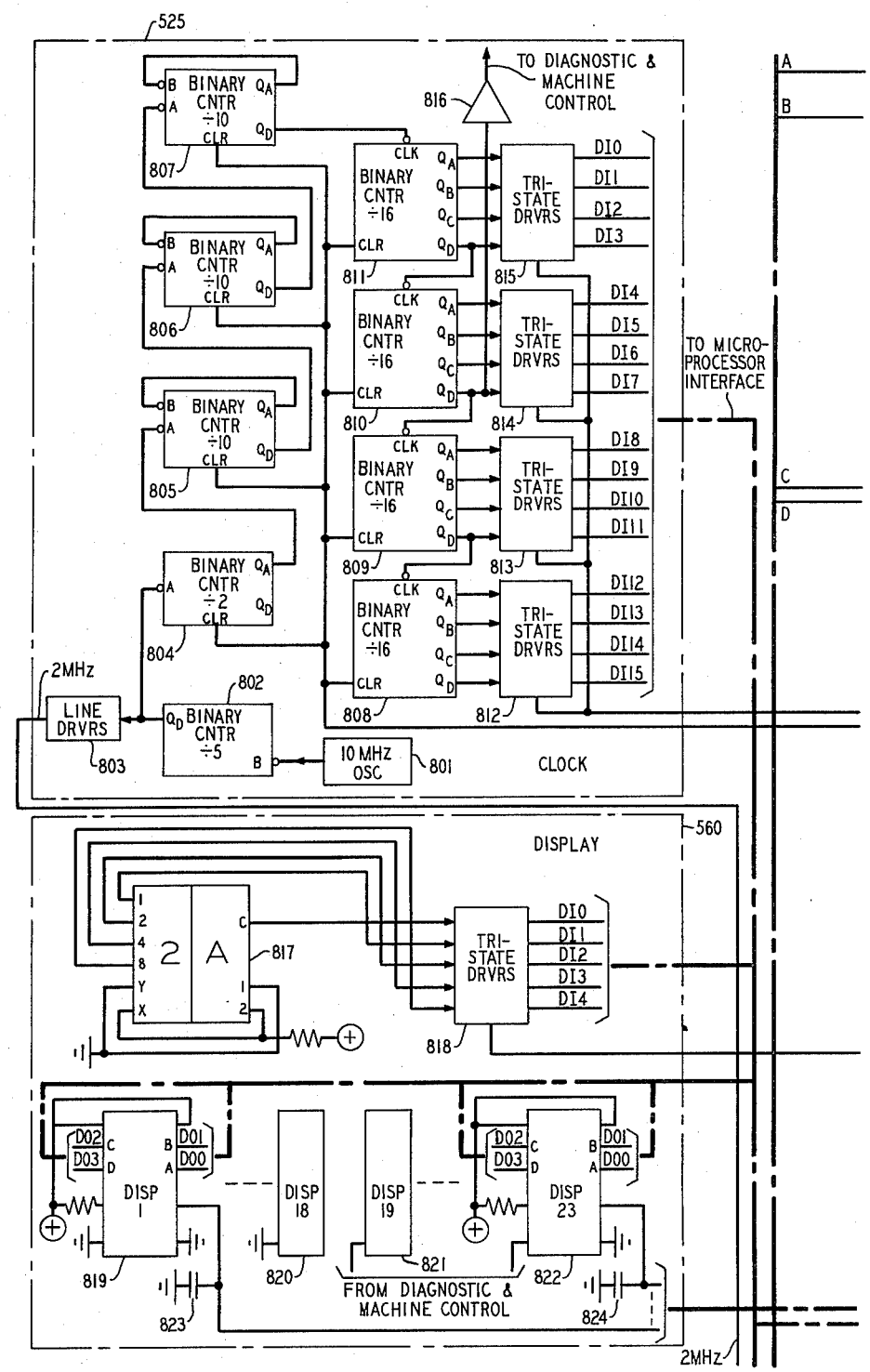

Clock 525, as shown in detail in FIG. 8, provides the basic timing signals used for data collection. Clock 525 includes a 10 megahertz crystal oscillator 801. An example of a crystal oscillator suitable for this purpose is a model CO-238B oscillator manufactured by Vectron Laboratories, Inc. The output of oscillator 801 is coupled to binary counter 802 which effects a frequency division by a factor of five to produce a two megahertz signal. This two megahertz signal is coupled via line driver 803 to period monitor 518 for use therein as described previously.

The two megahertz signal out of binary counter 802 also is fed to binary counters 804 through 807 which perform a further frequency reduction. In particular, the output signal available from binary counter 807 has a frequency of one kilohertz. The one kilohertz signal from binary counter 807 is coupled to binary counters 808 through 811 which form a 16-bit counter capable of storing counts in one millisecond intervals.

It should be noted that clock 525 interacts through microprocessor 545 with Z-axis monitor control logic 530 to provide the times required to perform a given event. In addition, outputs from counters 808 through 811 are coupled to tristate drivers 812 to 815 which feed various timing signals via address logic 535 and I/O port 540 to microprocessor 545 upon command.

Line driver 816, which is coupled to the QD output of counter 810, is used to feed signals to diagnostic and machine control logic 570 and display 560. These signals cause the information presented on display 560 to blink.

3.3 Z-Axis Monitor Control Logic

Figure 11:
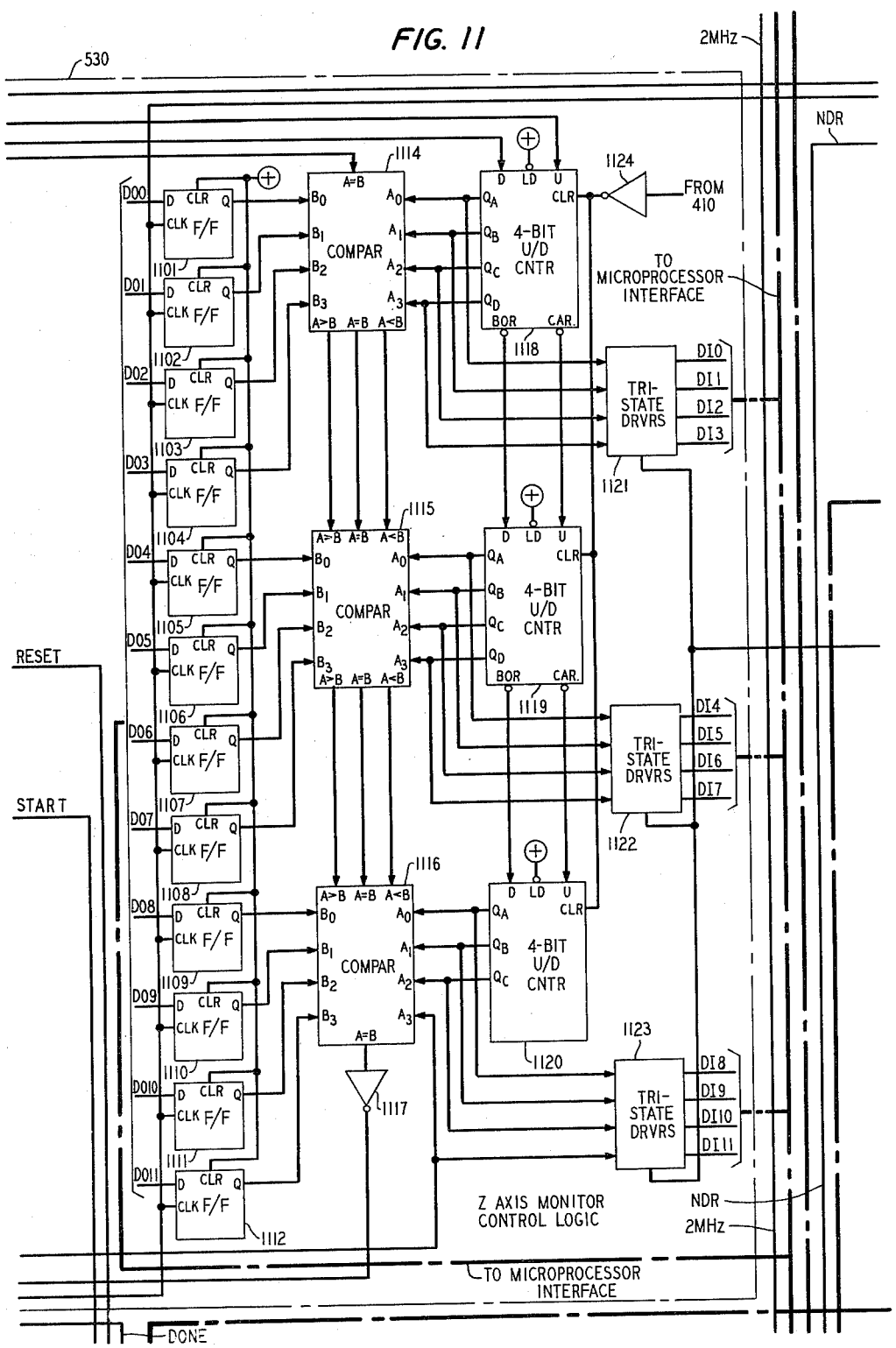

As noted previously, speed measurements of spindle 501 are made at a number of positions during the course of a drilling operation. These height positions, which are preset into microprocessor 545, are transferred from microprocessor 545 to Z-axis monitor control logic 530 and, in particular, to flip-flops 1101 through 1112 therein as shown in FIG. 11. The preset height position transferred to flip-flops 1101 through 1112 is updated three times during the course of a measurement for each hole drilled.

During each drill cycle, Z-axis monitor control logic 530 is reset to zero by a pulse from Z-axis monitor 410 which is coupled through inverter 1124 to up/down counters 1118 through 1120. This arrangement provides for an absolute zero reference and allows any noise signals which may have been coupled into up/down counters 1118 through 1120 to be cleared and the system to be re-referenced. Proceeding in this fashion, any accumulation of inaccuracies in the measurement of the height of spindle 501 are circumvented. Furthermore, a repeatable reference point for the location of drill spindle 501 during each measurement is provided.

Figure 10:
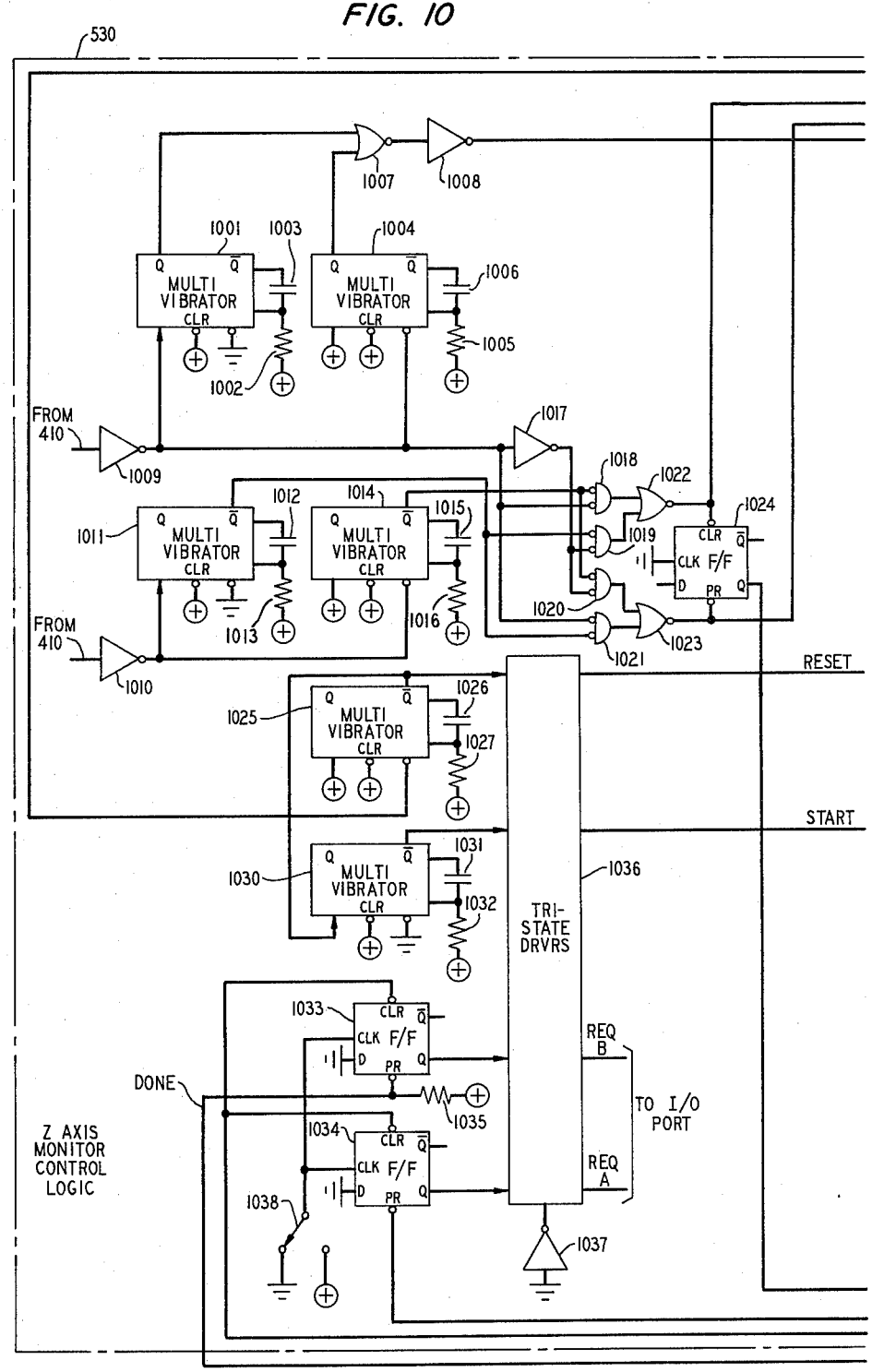

The actual vertical position and direction of spindle 501 are monitored by up/down counters 1118 through 1120. Outputs from counters 1118 through 1120 are compared continuously with the outputs of flip-flops 1101 through 1112 by comparators 1114 through 1116 during the course of a measurement. When a match is achieved, comparators 1114 through 1116 generate a pulse which is inverted in inverter 1117 and sent to flip-flop 1034, as shown in FIG. 10. This causes a REQ A pulse to be generated for subsequent use by microprocessor 545. A comparator suitable for this purpose is a Texas Instruments, Inc. comparator model SN74LS85.

Tristate drivers 1121 through 1123 which are coupled to the outputs of up/down counters 1118 through 1120 enable microprocessor 545 to monitor the actual height of spindle 501. The outputs from tristate drivers 1121 through 1123 are fed to microprocessor 545 through address logic 535 and I/O port 540.

During the course of a measurement, Z-axis monitor 410 provides three separate output signals. Two of these outputs are square wave signals in quadrature the period of which corresponds to approximately 0.8 of a mil. As the readers and light source within Z-axis monitor 410 move past a ruled grating, also internal to Z-axis monitor 410, an indication is produced of the height and direction of travel. These signals out of Z-axis monitor 410 are delivered to inverters 1009 and 1010 where they are inverted and fed to circuit elements 1011 through 1024 for decoding of the direction of travel information. Circuit elements 1011 through 1024 effectively steer the decoded direction information to either the up input or down input of up/down counters 1118 through 1120.

If the output from inverter 1009 is low, NAND gates 1018 and 1021 are partially enabled. Multivibrators 1011 and 1014 are configured so as to respond to positive going pulse transitions and negative going pulse transitions, respectively. Multivibrator 1011, for the input signals noted, produces an output pulse which completes the enablement of NAND gate 1021. The signal from NAND gate 1021 is coupled through NOR gate 1023 to up/down counters 1118 through 1120 and the count therein is decremented by one. Simultaneously, flip-flop 1024 is driven to a low logic level indicating the direction of travel.

For a negative going pulse transition, multivibrator 1014 is actuated. A signal from multivibrator 1014 completes the enablement of NAND gate 1018. This signal is coupled through NOR gate 1022 and enters up/down counters 1118 through 1120 as an upcount pulse. Simultaneously, the state of flip-flop 1024 is reversed indicating a change in the direction of travel of spindle 501.

When the output from inverter 1009 is a high logic level signal, the positive and negative going pulse transitions from inverter 1010 are coupled through multivibrators 1011 and 1014, NAND gates 1019 and 1020 and NOR gates 1022 and 1023 in a manner similar to that heretofore described. As a result of this signal processing, the correct up-down information is provided to up/down counters 1118 through 1120. It should be noted that in this instance NAND gates 1019 and 1020 are partially enabled by a signal from inverter 1017.

The timing of the signals produced by multivibrators 1011 and 1014 is controlled by capacitor 1012 and resistor 1013 and capacitor 1015 and resistor 1016, respectively.

In order to avoid any erroneous information being produced by comparators 1114 through 1116, comparisons are made of the data in up/down counters 1118 through 1120 with that stored in flip-flops 1101 through 1112 only when up/down counters 1118 through 1120 are not changing state. As noted previously, the state information is coupled through inverter 1009 and the pulse transition information is coupled through inverter 1010. Consequently, the pulse transitions out of inverter 1009 are 90 degrees out of phase with the pulse transitions out of inverter 1010. The pulse transitions out of inverter 1009 are used to generate either positive pulses out of multivibrator 1001 or negative pulses out of multivibrator 1004. Resistor 1002 and capacitor 1003 control the width of the pulse generated by multivibrator 1001. Similarly, resistor 1005 and capacitor 1006 control the width of the pulse generated by multivibrator 1004.

Once either the positive or negative pulse is generated, it is coupled through NOR gate 1007 and inverter 1008 and fed to comparators 1114 through 1116 thereby actuating them and causing a comparison to be made.

When a comparison is made, the REQ A pulse generated as described previously, and forwarded to microprocessor 545, the latter generates a status word which is coupled to decoder 910. Upon the receipt of a pulse from decoder 910, shown in FIG. 9, multivibrator 1025, shown in FIG. 10, is actuated. The width of the pulse generated by multivibrator 1025 is controlled by capacitor 1026 and resistor 1027. This pulse is coupled out of multivibrator 1025 on a lead labeled RESET and serves to reset period monitor 518. The RESET signal out of multivibrator 1025 is also coupled to multivibrator 1030. Multivibrator 1030 provides some delay before generating a START pulse. The amount of this delay is controlled by capacitor 1031 and resistor 1032. Application of the START pulse to period monitor 518 causes the count therein to be initialized. The REQ A signal also causes the time in clock 525 to be read or the clock to be reset to zero along with the initiation of a code for generating a new START pulse if one is needed.

Finally, when a spindle speed measurement is completed, a pulse is coupled from period monitor 518 via a lead labeled DONE to flip-fop 1033. Actuation of flip-flop 1033 causes a REQ B signal to be generated.

Resistor 1035 is a dropping resistor for fixing the voltage level applied to flip-flop 1033. Switch 1038 is a schematic representation of an initialization switch. In actuality this function is provided by microprocessor 545.

3.4 Display

Display 560, which is shown in more detail in FIG. 8, is comprised of 23 separate display modules such as modules 819 through 822. Each of these modules has internal thereto a decoder and driver which enable the synthesis of a hexadecimal display. An example of a display module suitable for this purpose is a Dialco display unit model number 745-0007.

To load data from microprocessor 545 into display 560, the data to be displayed is presented to display modules 819 through 822 on output lines DO0 through DO3. The selection of which display module is to receive the data is effected by transmitting a display address on output lines DO8 through DO12 coupled to decoders 931 through 933 shown in FIG. 9. Decoders 931 through 933 decode this display address and actuate one of 23 separate output lines, one for the load input of each of the 23 separate display modules 819 through 822. A capacitor such as capacitor 823 or 824 is coupled to each display module for filtering out any noise which might appear at the display module.

As noted previously, the information which is presented on display 560 includes the spindle identification, the number of holes drilled with that spindle, the amount of energy expended in drilling the most recent hole with that spindle, and certain diagnostic information.

Also included in display 560 is a display select switch 817. This switch enables an operator to select which of the above information is to be displayed for a given spindle 501. Once the operator manually selects this information, it is presented to tristate drivers 818 for transmission to microprocessor 545 over leads DI0 through DI4.

3.5 Diagnostic and Machine Control Logic

When the drilling energy, as determined by microprocessor 545, is found to be outside some predetermined limits, various inferences can be made. For example, if the amount of energy expended is too low, it can be inferred that drill bit 502 is broken. On the other hand, if the amount of expended energy is too high, it can be inferred that drill bit 502 is worn excessively.

In either case a message is sent to the last five digits of display 560 indicating the spindle identification and the cause of the defect. These digits are then caused to blink to alert the drilling machine operator. Simultaneously, the drilling machine is shut down until such time as corrective measures are taken. Implementation of these functions is accomplished by diagnostic and machine control logic 570.

Upon receipt of a status word from microprocessor 545, examples of which are shown in FIG. 15, the instruction is decoded in decoder 1440 thus causing the loading of an output signal on line DO1 into flip-flop 1441. Flip-flop 1441, shown in FIG. 14, then changes state and produces a signal which is applied to AND gate 1350, shown in FIG. 13, thereby partially enabling it. The enablement of AND gate 1350 is completed by the application of a timing signal from inverter 816 in clock 525. With AND gate 1350 enabled, the output therefrom is inverted by inverter 1351 and applied to the last five digits in display 560. In particular, the output from inverter 1351 is applied to display modules 821 and 822. This signal causes the display of the last five digits to blink on and off.

Simultaneously, the signal from flip-flop 1441 is applied to a Darlington pair circuit comprised of transistors 1354 and 1355. Actuation of the Darlington pair causes the opening of normally closed relay 1352. With relay 1352 opened the drilling machine is stopped. It should be noted also that the drilling machine can be controlled manually by switch 1353.

3.6 Calibration Circuit

Figure 14:
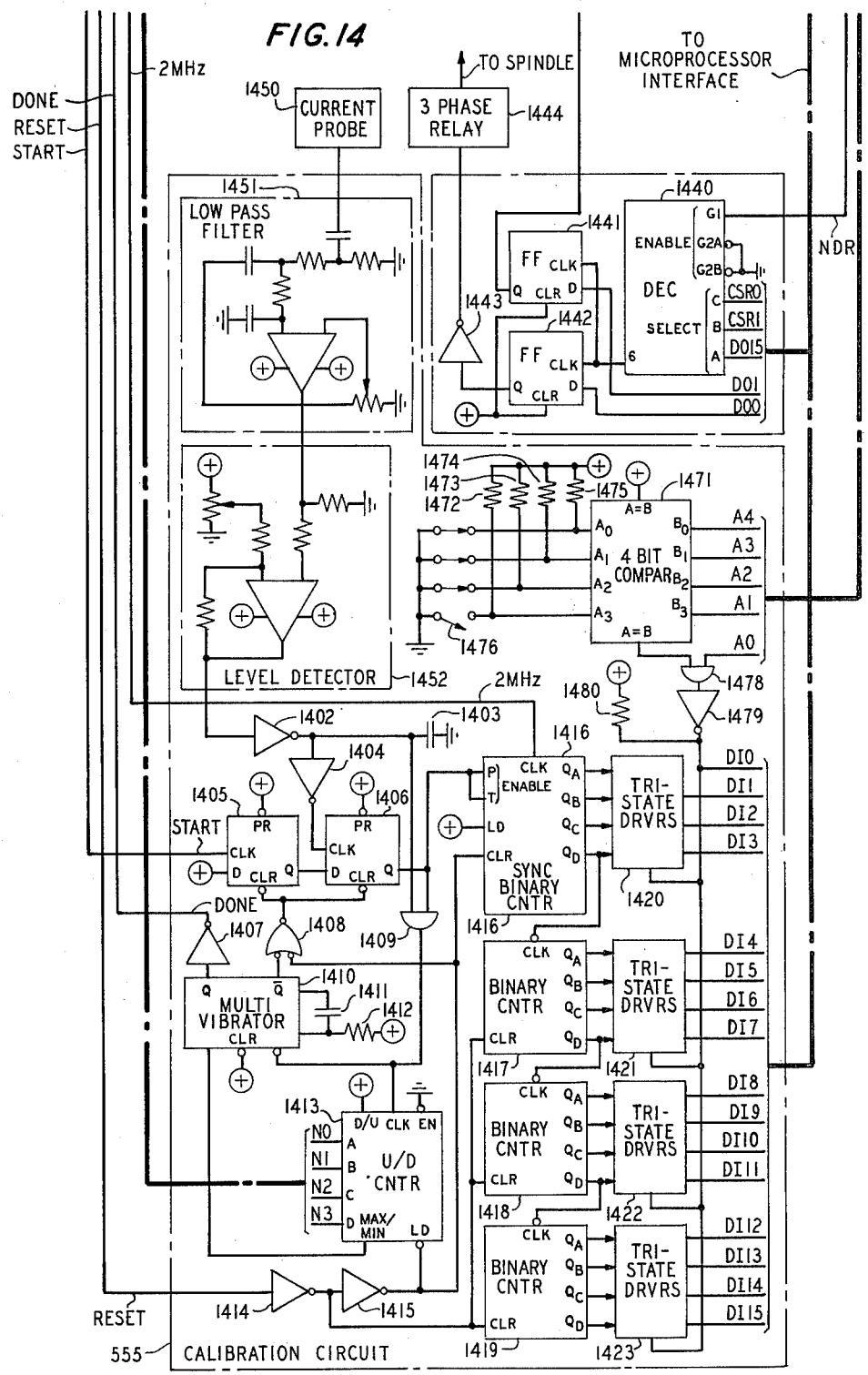

Calibration circuit 555, shown in FIG. 14, is used to measure the frequency of the drive current applied to each of spindles 501. The difference in frequency between the drive current and the rotational frequency of spindle 501 is termed "slippage." A measure of this "slippage" is used to calibrate spindle 501.

Measurement of the frequency of the spindle drive current is effected with current probe 1450. The output from current probe 1450 is applied to low pass filter 1451 which limits the amount of noise in the signal path. Thereafter the signal is applied to level detector 1452. Level detector 1452 converts the AC signal from current probe 1450 and low pass filter 1451 into a TTL compatible signal having the same frequency as the drive current. The period of the signal from level detector 1452 is ascertained by circuit elements 1402 through 1423. These elements operate in the same manner as elements 1302 through 1323 in period monitor 518. In addition, comparator 1471, resistors 1472 through 1475, switch 1476 and elements 1478 through 1480 function in an identical manner to comparator 911, resistors 912 through 915, switch 916 and elements 917 through 924. The operation of these latter elements will be described in the context of the address logic function. Hence, no further discussion with regard to the operation of these elements is necessary.

3.7 Address Logic

Address logic 535 routes the various signals from microprocessor 545 to other circuits in the system for implementation. In general, microprocessor 545 has three 16-bit data words available for communication with the other circuits. These data words are referred to as an input word, an output word, and a status word. The input and output words carry data to and from microprocessor 545 and the other circuits in the drill monitor system. The status word and one line of the output word, DO15, are used to effect various control functions between the drill monitor circuits and microprocessor 545.

With respect to the control function, the principal commands are coupled from microprocessor 545 via parallel leads labeled CSR0, CSR1 and DO15. The binary information to be carried on these leads is set by microprocessor 545. The table shown in FIG. 15 illustrates the various combinations of commands available using these three leads. Microprocessor 545 sets an appropriate bit pattern depending upon the function to be performed. For example, if the height register comprised of flip-flops 1101 through 1112 is to be loaded, microprocessor 545 would set CSR0 to zero, CSR1 to one and DO15 to zero. The actual height to be loaded would be fixed into the output word with eleven bits being used for magnitude and one bit being used for direction.

To effect the loading, a decoder 910, such as a Texas Instruments, Inc. model SN74LS138, upon receipt of a new data ready (NDR) pulse, decodes the status word to ascertain the function to be performed. In this instance a signal is produced at an output labeled "2" of decoder 910. This signal is coupled to the CLK inputs of flip-flops 1101 through 1112 to effect loading of the height data appearing on lines DO0 through DO11 into the height register.

Another function initiated by the decoding of a status word by decoder 910 is the generation of a START pulse by multivibrator 1025. The signal appearing on the output labeled "3" of decoder 910 is used for this purpose. It should be recalled that the production of a START pulse causes period monitor 518 to begin the rotational speed measurement of spindle 501.

Figure 12:
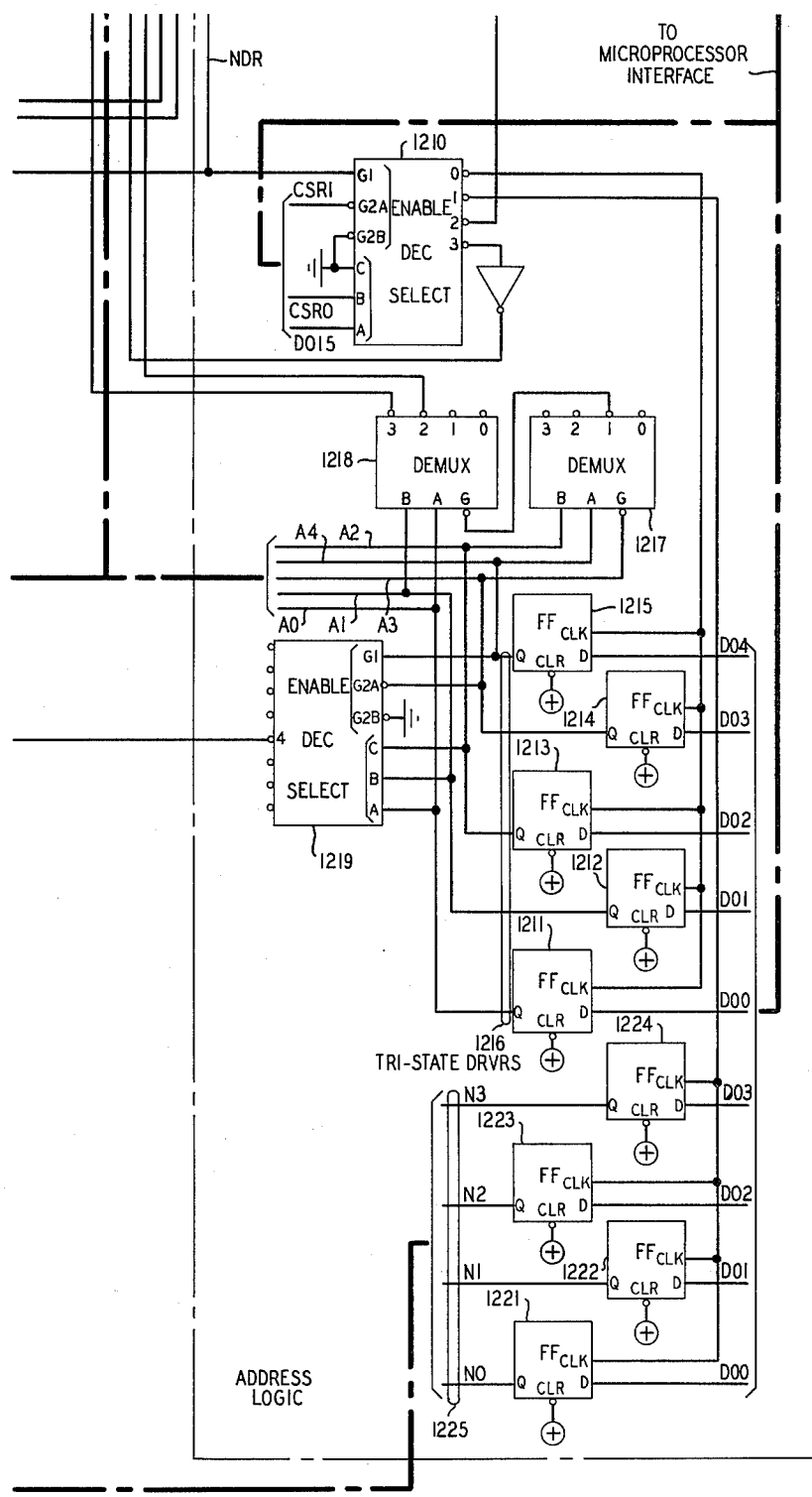

Decoder 1210, as shown in FIG. 12, decodes a control word from microprocessor 545 to produce a command to transfer the spindle address to flip-flops 1211 through 1215 for storage. This command is provided at an output labeled "0". Other functions implemented by the decoding of this control word by decoder 1210 are the loading of the number of spindle revolutions to be used for the spindle rotational speed measurement, the loading of the data to be displayed into display 560, and the resetting of clock 525 to zero. Signals to provide these functions appear at outputs of decoder 1210 which are labeled "1", "b" and "3", respectively.

More specifically, with a signal appearing at output "0" of decoder 1210, flip-flops 1211 through 1215 are loaded with the data appearing on lines DO0 through DO4 from microprocessor 545. This address is used to select which data are to be presented in the input word to microprocessor 545. The outputs of flip-flops 1211 through 1215 are fed to tristate drivers 1216, which direct the flow of data to the input word of microprocessor 545. This address stored in flip-flops 1211 through 1215 facilitates the placement of the spindle data in the input word through a comparison effected by comparator 911 with switch settings selected by switch elements 912 through 916.

Figure 9:
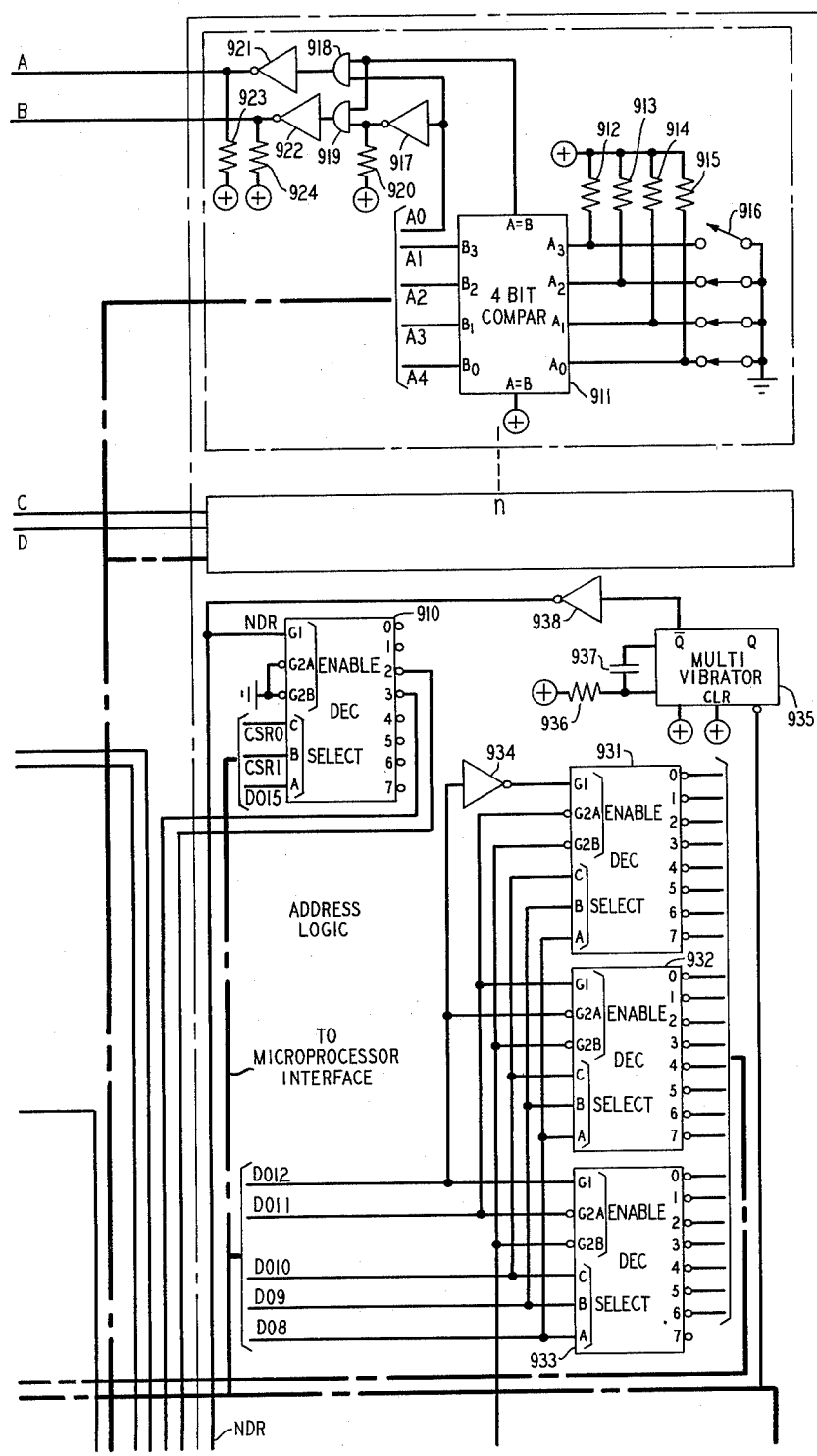

As noted previously, each spindle 501 has a separate period monitor 518 associated therewith. However, for economy of system fabrication, two period monitors 518 are contained on a given circuit card. In order to select the proper period monitor 518, the address must be further decoded. This decoding is partially effected by comparator 911, as shown in FIG. 9, and particularly by output A0 coupled therefrom. Data on line A0 is fed to circuit elements 917 through 924 where a selection is effected as to which period monitor 518 is to be accessed. Specifically, if a match results from the comparison made by comparator 911, an output signal appears at the A=B output. This signal partially enables AND gates 918 and 919. The signal on the A0 line completes the enablement of AND gate 918 or, following inversion by inverter 917, completes the enablement of AND gate 919. In both cases the signals out of AND gates 918 and 919 are inverted by inverters 921 and 922, respectively, to select the appropriate period monitor 518 to be accessed. This selection signal either appears on a lead labeled A or a lead labeled B. It should be noted that resistors 920, 923 and 924 are merely pull-up resistors for inverters 917, 921 and 922, respectively.

The outputs from tristate drivers 1216, as shown in FIG. 12, are also used to control an instruction for putting the clock time on the input word to microprocessor 545. Outputs from tristate drivers 1216 are coupled to demultiplexers 1217 and 1218. Output "3" of demultiplexer 1218 causes data set on display select switch 817, shown in FIG. 8, to be coupled to tristate drivers 818 and thence to microprocessor 545 over leads labeled DI0 through DI4. Output "2" from demultiplexer 1218 actuates tristate drivers 812 through 815 to couple the time data from clock 525 to microprocessor 545 on leads labeled DI0 through DI15.

Address lines A0 through A4 are also coupled to decoder 1219, shown in FIG. 12. Decoding accomplished by decoder 1219 permits data on the Z-axis monitor height to be coupled to microprocessor 545 via leads labeled DI0 through DI11. The output from decoder 1219 effects this transfer of data by triggering tristate drivers 1121 through 1123 shown in FIG. 11.

Flip-flops 1221 through 1224 store data indicating the number of revolutions of spindle 501 which are to be sampled for a given period measurement. This data is coupled from microprocessor 545 to flip-flops 1221 through 1224 via leads labeled DO0 through DO3 upon the application of a pulse from output "1" of decoder 1210. Subsequently, this data is applied to up/down counter 1313 in period monitor 518.

When data is ready to be received from microprocessor 545, multivibrator 935 receives a new data ready signal from microprocessor 545 and reconstitutes it with some fixed delay controlled by resistor 936 and capacitor 937. Following the preselected delay, the signal is coupled to various other circuits in the system to actuate them so that data appearing on input lines of these circuits is coupled into them to facilitate implementation of the desired function.

Finally, it should be noted that decoder 1440, shown in FIG. 14, decodes data from microprocessor 545 in order to control, via flip-flop 1442 and inverter 1443, the actuation of spindle relay 1444. Spindle relay 1444 controls the drive power applied to spindle 501.

In all cases it is to be understood that the above-described embodiment is illustrative of but a small number of many possible specific embodiments which can represent applications of the principles of the invention. Thus, numerous and various other embodiments can be devised readily in accordance with these principles by those skilled in the art without departing from the spirit and scope of the invention.

I claim:

1. A method for ascertaining the wear of a drill bit during the performance of a drilling operation on a workpiece comprising the steps of:
    monitoring with a position monitoring device positions of said drill bit prior to engagement with and after emergence from said workpiece;
    determining a first rotational speed of said drill bit at the position indicated by said position monitoring device prior to engagement with said workpiece;
    storing temporarily said first rotational speed of said drill bit;
    determining a second rotational speed of said drill bit at the position indicated by said position monitoring device following emergence of said drill bit from said workpiece;
    measuring the elapsed time between said first and second rotational speed determinations;
    determining the amount of energy expended during said drilling operation from said first and second rotational speed determinations and said elapsed time; and
    generating a measure of the wear of said drill bit from said energy determination.

2. The method in accordance with claim 1 wherein said position monitoring step further includes the steps of:
    storing temporarily a predetermined height position of said drill bit spaced apart from said workpiece;
    measuring an actual height position of said drill bit with respect to said workpiece;
    monitoring said actual measured height position and a direction of travel of said drill bit with respect to said workpiece;
    decoding direction of travel information so that said actual measured height position is decremented by a predetermined unit of height as said drill bit approaches said workpiece and is incremented by a predetermined unit of height as said drill bit recedes from said workpiece;
    comparing said actual measured height position of said drill bit with respect to said workpiece and said predetermined height position of said drill bit spaced apart from said workpiece; and
    generating an output signal when said actual measured height position and said predetermined height position correspond.

3. The method in accordance with claim 1 wherein said rotational speed determining step further includes the steps of:
    illuminating with light energy a spindle having affixed therein said drill bit;

absorbing a first portion of said light energy by light energy absorbing means which extend approximately halfway around the circumference of said spindle and adhere thereto;

detecting a second portion of said light energy reflected from said spindle in a region adjacent that having said light energy absorbing means adhering thereto;

counting a number of transitions occurring between said reflected light energy and said absorbed light energy; and measuring, concurrently with said counting step, an elapsed time corresponding to said number of transitions.

4. Apparatus for ascertaining the wear of a drill bit during the performance of a drilling operation on a workpiece, the apparatus including:

means for monitoring positions of said drill bit prior to engagement with said workpiece and after emergence from said workpiece;

means, responsive to said position monitoring means, for determining a first rotational speed of said drill bit at the indicated position prior to engagement with said workpiece and a second rotational speed of said drill bit at the indicated position after emergence from said workpiece;

means for storing temporarily said first rotational speed of said drill bit;

means for measuring an elapsed time between said first and second rotational speeds;

means, responsive to said speed determining means, said rotational speed storing means and said time measuring means, for determining the amount of energy expended during said drilling operation based on said first and second rotational speeds and said elapsed time, said means further generating a measure of the wear of said drill bit based on said energy determination.

5. The apparatus in accordance with claim 4 wherein said position monitoring means comprises:

means for storing temporarily a predetermined height position of said drill bit spaced apart from said workpiece;

means for measuring an actual height position of said drill bit with respect to said workpiece;

means, responsive to said height position measuring means, for monitoring said actual measured height position and a direction of travel of said drill bit with respect to said workpiece;

means, responsive to said height position measuring means, for decoding direction of travel information so that said actual measured height position is decremented by a predetermined unit of height as said drill bit approaches said workpiece and is incremented by a predetermined unit of height as said drill bit recedes from said workpiece;

means, responsive to said actual measured height position monitoring means and said predetermined height position storing means, for comparing said actual measured height position of said drill bit with respect to said workpiece and said predetermined height position of said drill bit spaced apart from said workpiece; and means, internal to said comparing means, for generating an output signal when said actual measured height position and said predetermined height position correspond.

6. The apparatus in accordance with claim 5 wherein said predetermined height position storing means comprises:

a plurality of flip-flops arranged in parallel; and means for coupling a multibit digital signal representing said predetermined height position to said plurality of flip-flops such that separate bits in said signal are coupled to separate flip-flops.

7. The apparatus in accordance with claim 5 wherein said actual measured height position monitoring means comprises:

a plurality of up/down counters each having a separate input for an up-count signal and a separate input for a down-count signal and each counter further having a separate output for a borrow signal and a separate output for a carry signal; and means for coupling said counters to one another such that said borrow signal output is coupled to said down-count signal input and said carry signal output is coupled to said up-count signal input.

8. The apparatus in accordance with claim 5 wherein said direction of travel information decoding means comprises:

first, second and third inverters, said first inverter output coupled to said third inverter input;

first and second multivibrators each of which has an input coupled to an output of said second inverter;

means for controlling the time duration of signals produced by said first and second multivibrators;

first, second, third and fourth NAND gates each of which has a pair of inputs, said first NAND gate inputs coupled to said first inverter output and said second multivibrator output, said second NAND gate inputs coupled to said first multivibrator output and said third inverter output, said third NAND gate inputs coupled to said second multivibrator output and said third inverter output, and said fourth NAND gate inputs coupled to said first inverter output and said first multivibrator output;

first and second NOR gates, each of which has a pair of inputs, said first NOR gate inputs coupled to said first and second NAND gate outputs and said second NOR gate inputs coupled to said third and fourth NAND gate outputs; and a flip-flop having first and second inputs coupled to said first and second NOR gate outputs, respectively.

9. The apparatus in accordance with claim 4 wherein said speed determining means comprises:

means for illuminating with light energy a spindle having affixed therein said drill bit;

means, extending approximately halfway around the circumference of said spindle and adhering thereto, for absorbing a first portion of said light energy produced by said illuminating means;

means for detecting a second portion of said light energy produced by said illuminating means which energy is reflected from said spindle in a region adjacent that having said absorbing means adhering thereto;

means for counting a number of transitions occurring between said reflected light energy and said absorbed light energy; and means for measuring an elapsed time corresponding to said number of transitions.

10. The apparatus in accordance with claim 9 wherein said elapsed time measuring means comprises:

clock means; and means, responsive to said clock means, for accumulating a number of clock pulses corresponding to said number of transitions.

11. The apparatus in accordance with claim 10 wherein said counting means comprises:
means for storing temporarily a number of spindle revolutions to be sampled; and
means, responsive to said number of spindle revolutions storing means, for controlling the number of clock pulses accepted by said accumulating means.

12. The apparatus in accordance with claim 11 wherein said number of spindle revolutions storing means comprises:
an up/down counter;
means for coupling a binary representation of said number of spindle revolutions to be sampled to said up/down counter; and
means for controlling the loading of said binary representation of said number of spindle revolutions to be sampled into said up/down counter.

13. The apparatus in accordance with claim 11 wherein said clock pulse controlling means comprises:
a multivibrator having an input coupled to said number of spindle revolutions storing means;
a NOR gate having a pair of inputs one of which is coupled to a first output from said multivibrator and the other of which is coupled to said means for controlling the loading of said binary representation of said number of spindle revolutions to be sampled into said up/down counter;
first and second flip-flops coupled to an output of said NOR gate and to each other; and
a two input AND gate, one input coupled to said reflected light energy detecting means and the other input coupled to an output of said second flip-flop, said AND gate being enabled during a time interval encompassing said number of spindle revolutions to be sampled and disabled when a counted number of spindle revolutions equals the number of such revolutions to be sampled thereby causing said multivibrator and said first and second flip-flops to change state and disable said synchronous binary counter in said accumulating means.

14. The apparatus in accordance with claim 10 wherein said accumulating means comprises:
a synchronous binary counter; and
a plurality of binary counters coupled in tandem with each other and with said synchronous binary counter.

15. The apparatus in accordance with claim 10 wherein said clock means comprises:
an oscillator; and
a plurality of binary counters connected in tandem with said oscillator.

16. The apparatus in accordance with claim 4 further including:
display means; and
means for selecting which spindle out of n spindles is to have selected information associated therewith presented on said display means.

17. The apparatus in accordance with claim 4 further including:
means for calibrating a spindle, said calibrating means comprising
a current probe;
a low-pass filter coupled in series with said current probe;
a level detector coupled in series with said low-pass filter;
means for storing temporarily a number of spindle revolutions to be sampled;
clock means;
means for accumulating a number of clock pulses produced by said clock means; and
means, responsive to said number of spindle revolutions storing means and coupled to said level detector, for controlling the number of clock pulses accepted by said accumulating means.

18. The apparatus in accordance with claim 17 wherein said number of spindle revolutions storing means comprises:
an up/down counter;
means for coupling a binary representation of said number of spindle revolutions to be sampled to said up/down counter; and
means for controlling the loading of said binary representation of said number of spindle revolutions to be sampled into said up/down counter.

19. The apparatus in accordance with claim 18 wherein said clock means comprises:
an oscillator; and
a plurality of binary counters connected in tandem with said oscillator.

20. The apparatus in accordance with claim 19 wherein said accumulating means comprises:
a synchronous binary counter; and
a plurality of binary counters coupled in tandem with each other and with said synchronous binary counter.

21. The apparatus in accordance with claim 20 wherein said clock pulse controlling means comprises:
a multivibrator having an input coupled to said number of spindle revolutions storing means;
a NOR gate having a pair of inputs one of which is coupled to a first output from said multivibrator and the other of which is coupled to said means for controlling the loading of said binary representation of said number of spindle revolutions to be sampled into said up/down counter;
first and second flip-flops coupled to an output of said NOR gate and to each other; and
a two input AND gate, one input coupled to said reflcted light energy detecting meand and the other input coupled to an output of said second flip-flop, said AND gate being enabled during a time interval encompassing said number of spindle revolutions to be sampled and disabled when a counted number of spindle revolutions equals the number of such revolutions to be sampled thereby causing said multivibrator and said first and second flip-flops to change state and disable said synchronous binary counter in said accumulating means.

* * * * *

UNITED STATES PATENT AND TRADEMARK OFFICE
CERTIFICATE OF CORRECTION

PATENT NO. : 4,228,514
DATED : October 14, 1980
INVENTOR(S) : Roger E. Weiss

It is certified that error appears in the above—identified patent and that said Letters Patent is hereby corrected as shown below:

Column 2, line 25, "is" should read --it--. Column 5, line 55, "n" should read --$\underline{n}$--; line 57, "n" should read --$\underline{n}$--. Column 6 line 7, "j" should read --$\underline{j}$--; line 8, "k" should read --$\underline{k}$--; line 46, "than" should read --then--. Column 7, line 24, "n" should read --$\underline{n}$--. Column 9, line 52, "j" should read --$\underline{j}$--; line 58, "j" should read --$\underline{j}$--. Column 12, line 36, "flip-fop" should read --flip-flop--. Column 14, line 65, " "b" " should read --"2"--. Column 19, line 61, "n" should read --$\underline{n}$--. Column 20, line 53, "reflcted" should read --reflected--; and "meand" should read --means--.

Signed and Sealed this

Twenty-ninth Day of June 1982

[SEAL]

Attest:

GERALD J. MOSSINGHOFF

Attesting Officer

Commissioner of Patents and Trademarks